United States Patent [19]
Warren et al.

[11] Patent Number: 5,156,147
[45] Date of Patent: Oct. 20, 1992

[54] VARIABLE RATE PACEMAKER HAVING UPPER RATE LIMIT GOVERNOR BASED ON HEMODYNAMIC PERFORMANCE

[75] Inventors: Jay A. Warren, Camino, Calif.; Jay O. Millerhagen; Julio C. Spinelli, both of Shoreview, Minn.

[73] Assignee: Cardiac Pacemakers, Inc., St. Paul, Minn.

[21] Appl. No.: 651,318

[22] Filed: Feb. 5, 1991

[51] Int. Cl.$^5$ .............................................. A61N 1/00
[52] U.S. Cl. ......................................... 128/419.0 PG
[58] Field of Search ........ 128/419 PG, 419 P, 419 D, 128/734

[56] References Cited
U.S. PATENT DOCUMENTS

| | | | |
|---|---|---|---|
| 4,708,143 | 11/1987 | Schroeppel | 128/419 PG |
| 4,901,725 | 2/1990 | Nappholz et al. | 128/734 |
| 5,040,535 | 8/1991 | Mann et al. | 128/419 PG |
| 5,092,339 | 3/1992 | Geddes et al. | 128/734 |

OTHER PUBLICATIONS

Geddes, L. A., "The Next Generation Pacemaker", *PACE,* vol. 13, pp. 131-133, Feb. 1990.
Wessale, Jerry L.; Voelz, Margaret B.; Geddes, Leslie A., "Stroke Volume and the Three Phase Cardiac Output Rate Relationship with Ventricular Pacing", *PACE,* vol. 13, pp. 673-680, May 1990.
Wessale, Jerry L.; Geddes, Leslie A.; Fearnot, Neal E.; Janas, Wolfgang; Grote, Lee Ann, "Cardiac Output Versus Pacing Rate at Rest with Exercise in Dogs with AV Block", *PACE,* vol. 11, pp. 575-581; May 1988.

*Primary Examiner*—Kyle L. Howell
*Assistant Examiner*—George Manuel
*Attorney, Agent, or Firm*—Haugen and Nikolai

[57] ABSTRACT

A rate adaptive pacemaker of the type having a variable rate cardiac stimulating pulse generator and a sensor for monitoring some physiologic parameter whereby the pulse generator stimulating rate can be adjusted to meet physiologic demand is further provided with a hemodynamic sensor which is operative to provide an output signal representing the pumping performance of the heart in response to the pacing stimulation. The signal from the hemodynamic sensor is processed and then used in an algorithm to determine whether further rate increase should be permitted based upon whether the rate increase would be accompanied by a further increase in cardiac output, a plateau or a decrease in cardiac output. Hence, the adaptive rate pacemaker is provided with a real-time, hemodynamic maximum pacing rate instead of a preprogrammed, fixed, maximum rate.

13 Claims, 2 Drawing Sheets

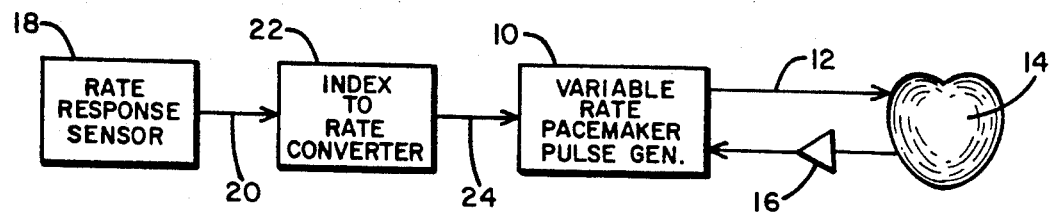
_Fig. 1_ PRIOR ART
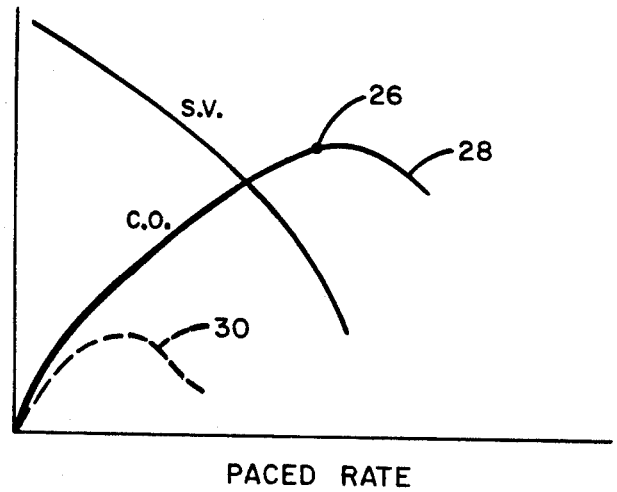
_Fig. 2_
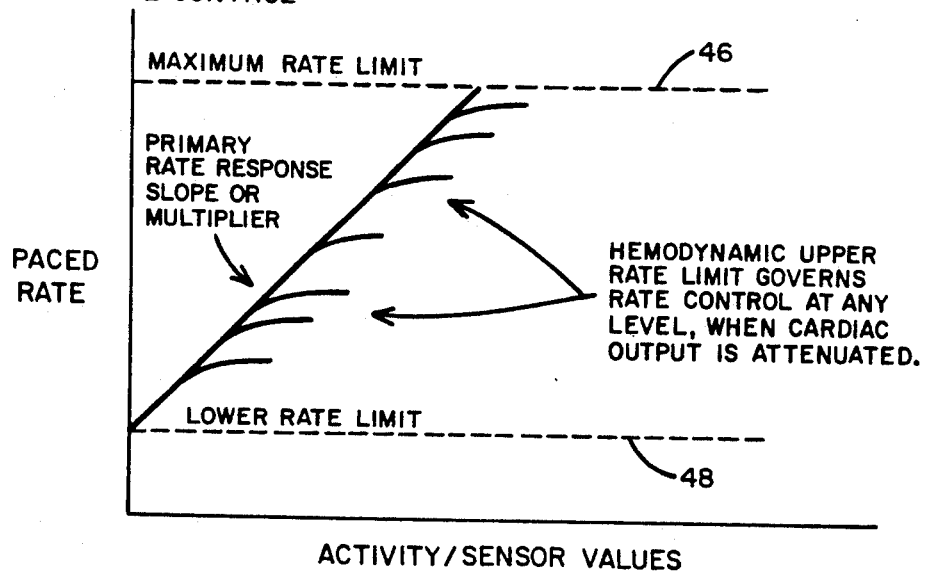
_Fig. 4_

VARIABLE RATE PACEMAKER HAVING UPPER RATE LIMIT GOVERNOR BASED ON HEMODYNAMIC PERFORMANCE

BACKGROUND OF THE INVENTION

I. Field of the Invention

This invention relates generally to cardiac pacing apparatus, and more particularly to a variable rate pacemaker which incorporates a sensor for monitoring hemodynamic performance and for establishing the pacing rate as determined by the hemodynamic performance of the heart.

II. Discussion of the Prior Art

There exists a class of cardiac pacemakers known as variable rate or rate adaptive pacemakers which include a first sensor for determining metabolic demand and means for adjusting the pacing rate or escape interval of the stimulating pulse generator based upon that metabolic demand. For example, the Anderson et al. U.S. Pat. No. 4,428,378 discloses a rate adaptive pacer having an activity sensor which produces an electrical signal related to the level of motion or activity of the patient in whom the pacemaker is implanted. The activity signal is signal-processed and applied to a voltage-controlled oscillator for adjusting the rate at which electrical stimulating pulses are produced. The pacemaker has a predetermined, programmed lower stimulating pulse rate, and sensed activity results in a pulse rate increase from that lower rate threshold up to a predetermined, programmed maximum rate.

There are a variety of other rate adaptive pacers in which parameters other than motion or activity are sensed. For example, the Begemann et al. U.S. Pat. No. 4,972,834 describes such a pacemaker in which the QT interval of the ECG cycle is measured and because that interval varies with physiologic demand, it is used to adjust the pacing rate or escape interval of a stimulating pulse generator such that the rate varies with physiologic demand. Again, a programmed lower rate limit and upper rate limit is provided to assure that the patient is not paced at a rate which may prove harmful. The upper rate limit is, however, established by the physician and programmed into the pacemaker as a fixed limit.

Other parameters that have been sensed and used to control pacing rate have included right ventricular systolic pressure (Koning et al. U.S. Pat. No. 4,566,456); blood pH (Alcidi U.S. Pat. No. 4,009,721); blood oxygen saturation (Wirtzfeld et al. U.S. Pat. No. 4,202,339); respiration rate (Krasner U.S. Pat. No. 3,593,718); partial pressure of carbon dioxide in the blood, $pCO_2$, (Koning et al. U.S. Pat. No. 4,716,887); blood temperature (Cook et al. U.S. Pat. No. 4,436,092); and pre-ejection period (Chirife U.S. Pat. No. 4,719,921).

The foregoing list of prior art patents relating to rate adaptive pacemakers is merely illustrative in that other patents have been granted. Hence, the above listing is not intended to be exhaustive.

Typical adaptive rate pacemakers, such as those described in the aforementioned patents, are primarily operated so as to increase the pacing rate in responses to a change in the parameter being sensed. However, if the pacing rate is allowed to increase inappropriately in a pathological heart, inefficiencies may result in the heart's pumping function, resulting in hemodynamic instability. That is to say, the patient may become uncomfortable, experience shortness of breath and cease exercising. Thus, it is desirable to establish a match between the pacing rate and the optimal pump function in that exercise tolerance would improve at both maximal and submaximal levels of effort.

Prior art adaptive rate pacemakers typically involve the simple conversion of a sensor value to a paced rate. The sensor index may be of various technologies, all as pointed out above. These technologies include piezoelectric motion or activity sensing, accelerometer-based activity, transthoracic impedance measures, right ventricular impedance measures and others. A study of prior art cardiac pacers also reveals that considerable attention has been paid to the establishment of rate response curves used to convert a sensor signal to a pacing rate control signal between the lower rate limits and maximum sensor rate. A combination of sensors may be used simultaneously or in concert for developing the desired rate response curve. For example, activity may be used to initiate rate response and a proportional control may be provided by sensing temperature or minute ventilation indices once the pacing rate has exceeded some predetermined value above the base or at-rest value. In accordance with the present invention, a pacemaker design and an algorithm is provided whereby the pacemaker is prevented from inducing hemodynamic failure due to an inappropriate pacing rate, which might otherwise result from conventional, prior art rate response algorithms. The apparatus and method of the present invention constitutes a departure from the prior art in that it offers a hemodynamic upper rate limit that minimizes the occurrence of hemodynamic instability arising from inappropriate pacing therapy. While conventional, prior art adaptive rate pacing devices have classicly used predetermined lower and maximum rate limits which are prescribed by the implanting physician, in accordance with the present invention a further sensor and/or algorithm is provided for quantifying hemodynamic performance and establishing an upper rate when it is determined that a further increase in pacing rate will result in a worsening of hemodynamic performance.

By adding a hemodynamic sensor to a rate adaptive pacer where the hemodynamic sensor quantifies the hemodynamic stability of the heart in response to pacing stimulation, the consequences of an inappropriately high pacing rate can be obviated. If the heart is paced too fast, it may not be able to adequately improve cardiac output. In a normal heart, at excessively high rates, the cardiac output decreases as the rate increases. This induced hemodynamic instability usually does not occur until there are higher paced rates, i.e., in excess of 150–200 bpm. However, in the pathologic heart, less cardiac reserve is present. Hence, if paced at too high a rate, severe shortness of breath and hemodynamic instability may result. While in prior art systems provision has been made for programming in an upper rate limit to control this problem, the present invention provides a way of optimally governing the upper rate limit or maximum sensor rate, based upon monitoring of the resulting hemodynamic performance of the heart.

OBJECTS

It is accordingly a principal object of the present invention to provide an improved rate adaptive cardiac pacemaker.

Another object of the invention is provide a rate adaptive cardiac pacemaker in which the upper rate limit is itself established by the use of a sensor and/or algorithm other than the one employed to develop the rate modifying control signal.

Yet another object of the invention is to provide a rate adaptive pacer having a hemodynamic performance based pacing rate governor.

Yet another object of the invention is to provide an improved rate adaptive pacemaker in which an algorithm is implemented for limiting pacing therapy when such therapy would result in a degradation of the heart's hemodynamic performance.

SUMMARY OF THE INVENTION

The foregoing objects are achieved in accordance with the present invention by providing a conventional rate adaptive pacemaker of the type including a variable rate pulse generating means for producing cardiac stimulating pulses, means for sensing a change in physiologic demand, means responsive to the sensed change in physiologic demand for providing a first control signal to the variable rate pulse generating means for varying the rate at which the stimulating pulses are produced. Added to that conventional arrangement is a further sensor responsive to the heart's hemodynamic performance. It produces second control signal which is operative to limit the maximum rate at which the stimulating pulses can be produced by the rate adaptive pacemaker. Thus, the hemodynamic performance may be assessed using, for example, intracardiac impedance plethysmography to measure cardiac output while an activity sensor is employed to sense physiologic demand and to alter the pacing rate. By incorporating an algorithm that determines whether a rate increase is accompanied by a corresponding increase in cardiac output, the pacing rate is allowed to increase. If, on the other hand, a call for an increase in pacing rate is accompanied by a decrease in cardiac output, then the rate increase is inhibited, thus establishing a real-time maximum pacing rate which is based upon hemodynamic performance of the heart rather than being a fixed programmed value established by the implanting physician.

DESCRIPTION OF THE DRAWINGS

The foregoing features, objects and advantages of the invention will become apparent to those skilled in the art from the following detailed description of the preferred embodiment, especially when considered in conjunction with the accompanying drawings in which:

FIG. 1 is a block diagram of a prior art adaptive rate pacemaker;

FIG. 2 is a graph showing the manner in which stroke volume and cardiac output vary with the pacing rate;

FIG. 4 is a graph illustrating the hemodynamically determined upper rate limit and the rate adaptive pacemaker of FIG. 3.

DESCRIPTION OF THE PREFERRED EMBODIMENT

Figure 3:
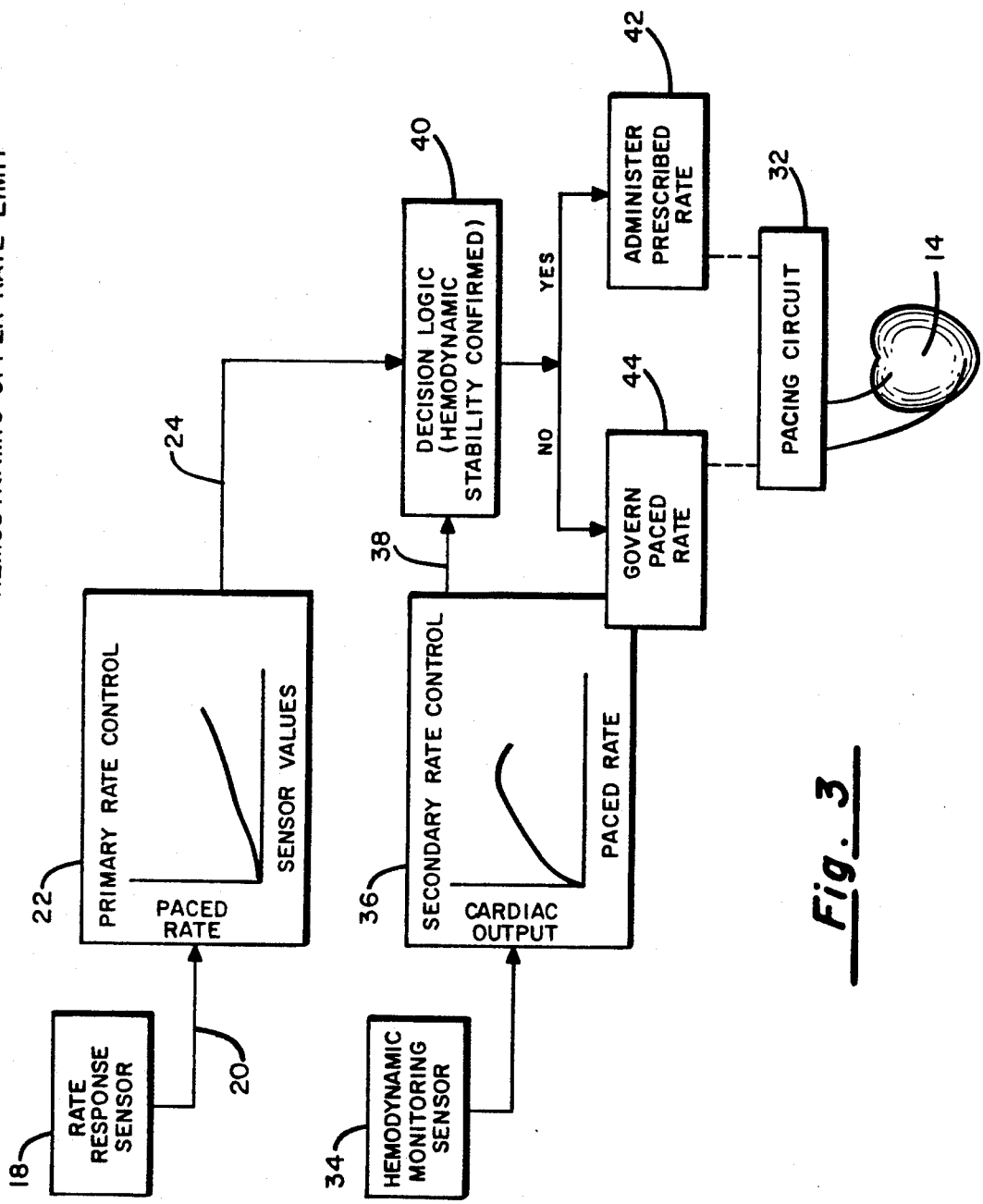
FIG. 3 is a block diagram representation of an adaptive rate pacemaker incorporating the hemodynamically determined maximum pacing rate in accordance with the present invention.

Before describing the rate adaptive pacemaker of the present invention, it is believed essential to a full and complete understanding thereof to first appreciate the features of prior art devices and, in this regard, reference is made to FIG. 1 which illustrates diagrammatically the functional components of such a device. It is seen to include a variable rate pacemaker pulse generator 10 capable of producing cardiac stimulating pulses on a lead 12 which is appropriately positioned on or in the heart 14. If the pulse generator 10 is of the demand type, a sense amplifier 16 would typically be used to detect normal cardiac depolarization signals (R-waves) and apply a reset to the timing circuits within the variable rate pacemaker pulse generator 10 to thereby preclude the generation of electrical stimulating pulses on lead 12 when the heart is beating in a normal fashion at a prescribed lower rate threshold.

Also forming a part of the prior art rate adaptive pacemaker is a rate response sensor 18 which, as already indicated, may take any number of forms depending upon the physiologic parameter to be monitored. For example, the sensor 18 may comprise a piezoelectric activity sensor, an accelerometer, a blood temperature sensor, a sensor for measuring rate and/or depth of respiration, or a sensor for monitoring a particular interval in the QRS complex, all as is disclosed in the prior art. In fact, the rate response sensor 18 may include plural sensors of different types to create a composite output which is piece-wise continuous so as to create an electric signal on line 20 indicative of physiologic demand. For example, between a lower limit and an intermediate rate value, activity may be sensed, and between that intermediate rate and a higher rate, blood temperature may be sensed. The electrical signal on line 20 is then applied to an index-to-rate convertor 22 for creating an electrical signal on line 24 which varies in a prescribed way with changes in the output from the rate's responsive sensor 18. This control signal on line 24 is then applied to the timing circuitry of the variable rate pacemaker pulse generator 10 to thereby vary the rate at which cardiac stimulating pulses are produced on lead 12.

Typically, the variable rate pacemaker pulse generator 10 will incorporate within it a lower rate limit and a maximum limit to place bounds on the stimulation pulse rate. The index-to-rate converter 22 operates to define the slope of the curve when the output signal therefrom is plotted as a function of the input signal on line 20 from the rate responsive sensor 18.

Referring next to FIG. 2, there is shown graphically a plot of both stroke volume and cardiac output as a function of the rate at which the heart is being paced. As the pacing rate increases, the stroke volume of the heart is seen to decrease. Cardiac output is the product of stroke volume and heart rate ($CO = SV \times HR$). It is seen to increase until a point is reached at which the stroke volume has fallen to such a low level that even though the paced rate increases, the cardiac output increases cannot be sustained. The use of a pacing rate higher than point 26 on the cardiac output curve 28 provides only a minimal increase in cardiac output. Hence, with a constant level of exercise, it would be inappropriate to choose a pacing rate greater than that associated with this point.

It should also be appreciated that a heart failure patient has low cardiac reserve, i.e., a diminished capacity of the heart to increase cardiac output and raise blood pressure above basal to meet body requirements. Hence, different levels of activity for such a patient will typically be inappropriate. If curve 28 is considered to be a plot of an individual with a healthy heart, the dotted line curve 30 may be representative of a patient with some degree of heart failure. While the maximum pacing rate is typically established by the cardiologist during the course of an exercise regimen, in accordance with prior art systems, that maximum rate is a fixed programmed value that could be inappropriate for higher levels of exercise and differing physiologic states.

In accordance with the present invention a hemodynamic sensor is added to the adaptive rate pacemaker which is operative to provide an output signal representing the pumping performance of the heart in response to the pacing stimulation. This signal is processed and then used in an algorithm to determine whether further rate increase should be permitted based upon whether the rate increase would be accompanied by: (1) a further increase in cardiac output,(2) a plateau or (3) a decrease in cardiac output. This provides a real-time, hemodynamic maximum pacing rate as contrasted to a pre-programmed fixed value.

Referring to FIG. 3, there is illustrated a block diagram of a rate adaptive pacer incorporating the hemodynamic maximum pacing rate aspects of the present invention. It includes the usual rate response sensor 18, an index-to-rate converter 22 resulting in a signal on line 24 which, if applied to the pacing circuit 32 will result in a change in the frequency with which stimulating pulses are applied to the heart 14. As already discussed, the rate control signal on line 24 is directly proportional to the change in physiologic demand sensed by the rate response sensor 18.

In addition to the rate response sensor 18, the rate adaptive pacemaker of the present invention also includes a hemodynamic monitoring sensor 34 which may comprise an impedance measuring system of the type described in the Salo et al. U.S. Pat. No. 4,686,987, the technology of which are hereby incorporated by reference. Further information concerning a pacemaker incorporating an impedance sensing system is the Citak et al. U.S. Pat. No. 4,773,401 assigned to applicants' assignee. Alternatively, the hemodynamic monitoring sensor 34 may measure right ventricular pressure or any other parameter indicative of the pumping performance of the heart. If a given sensor is used for the hemodynamic monitoring sensor 34, the rate response sensor 18 might well comprise the same physical sensor, e.g., impedance sensing sensor, a piezo-electric activity sensor, a blood temperature sensor or a respiration rate sensor. The algorithmic treatment of the sensor output would be different for the rate response than for the hemodynamic performance.

The output from the hemodynamic monitoring sensor 34 is likewise applied to an index-to-rate converter 36 operative to establish the transfer function between the pacing rate and the hemodynamic parameter being sensed. As is shown by block 36 in FIG. 3, for purposes of illustration, it is cardiac output that is the hemodynamic parameter being sensed by unit 34 and the device 36 produces a signal on line 38 relating cardiac output to the stimulating pulse rate (paced rate). This signal along with the one on line 24 from the index-to-rate converter 22 is applied to decision logic 40 which functions to determine whether hemodynamic stability is confirmed. The algorithm implementing the decision logic 40 determines whether the current cardiac output indicated by the signal on line 38 is higher or the same as it was for the previously established pacing rate and, if so, the pacing circuit 32 is allowed to again have its rate increased in accordance with the signal on line 24. On the other hand, if the decision logic 40 determines that the cardiac output indicated by the signal on line 38 is lower than the previously established value, then the signal on line 24 is prohibited from further increasing the stimulating pulse frequency of the pacing circuit 32.

Referring to FIG. 4, there is graphically illustrated the rate response of the pacemaker of the present invention with changes in the level of exercise or other physiologic parameter. While the pacemaker may have incorporated in it a programmed maximum sensor rate as indicated by dotted line 46 and a programmed lower rate limit 48, the hemodynamic upper rate limit governs the pacing rate at any level between these two limits when the decision logic 40 determines that cardiac output is attenuated with any further pacing rate increase.

For purposes of discussion, this invention has been described assuming a hemodynamic upper rate sensor 34 which uses right ventricular impedance based stroke volume measurements to calculate cardiac output. However, it is to be understood that this invention is not limited to this particular index, and may include any hemodynamic sensor, such as pressure, flow, volume, and/or timing components, such as pre-ejection interval, which may be appropriate to monitor cardiac performance. Further, the described embodiment presumed the use of conventional rate control using an activity based system, such as a piezo-electric crystal or an accelerometer. This invention is also not limited to that particular technology, and may include any sensor or multiplicity of sensors for driving the paced rate between a lower rate and an maximum rate.

While the invention has also been described assuming the hemodynamic stability confirmation is based upon a test as to whether an incremental increase in stimulating pulse rate is accompanied by a corresponding decrease in cardiac output, it is also possible, using a differentiating circuit to determine the rate of change of cardiac output with pacing rate and then inhibit further rate increases when the rate of change decreases with an incremental change in the pacing rate.

By using the present invention, the pacemaker of the present invention maximizes cardiac output at any given level of exercise while minimizing the symptomatic effect of pump malfunction resulting in exercise intolerance.

Those skilled in the art will appreciate that the present invention may be implemented in hardware in a variety of fashions. For example, a pacemaker incorporating the hemodynamic upper rate limit principle of the present invention can be implemented in analog circuitry or, conversely, the adaptive rate pacemaker may be implemented utilizing a programmable digital controller without departing from the spirit or scope of the invention. In fact, numerous changes may be made in the above-described apparatus and the different embodiments of the invention may be made without departing from the spirit thereof. Therefore, it is intended that all matter contained in the foregoing description and in the accompanying drawings shall be interpreted as illustrative and not in a limiting sense.

What is claimed is:

1. In a rate adaptive pacemaker of the type including a variable rate pulse generating means for producing cardiac stimulating pulses, means for sensing a change in a patient's physiologic demand, mans responsive to said sensed change in physiologic demand for providing a control signal to said variable rate pulse generating means to thereby alter the rate at which said stimulating pulses are produced by said variable rate pulse generating means, the improvement comprising:

(a) means for sensing changes in the hemodynamic performance of the heart in response to said stimulating pulses; and
(b) means responsive to said means for sensing changes in the hemodynamic performance for preventing said control signal from altering the rate at which said stimulating pulses are produced by said pulse generating means when to do so will compromise said hemodynamic performance of the heart.

2. The rate adaptive pacemaker as in claim 1 wherein said means for sensing changes in hemodynamic performance includes mans for measuring changes in right ventricular impedance.

3. The rate adaptive pacemaker as in claim 1 wherein said means for sensing changes in hemodynamic performance senses stroke volume.

4. The rate adaptive pacemaker as in claim 1 wherein said means for sensing changes in hemodynamic performance includes cardiac output sensing means.

5. The rate adaptive pacemaker as in claim 4 wherein said means for preventing inhibits said control signal from increasing the rate at which said stimulating pulses are produced when said cardiac output sensing means indicates that such a rate increase fails to cause a corresponding increase in cardiac output.

6. The rate adaptive pacemaker as in claim 1 wherein said means for sensing changes in hemodynamic performance includes means for measuring arterial pressures.

7. The rate adaptive pacemaker as in claim 1 wherein said means for sensing changes in hemodynamic performance includes means for means for measuring the pre-ejection interval of the cardiac cycle.

8. In a rate adaptive pacemaker of the type including a variable rate pulse generating means for producing cardiac stimulating pulses, means for sensing a change in physiologic demand, means responsive to said sensed change for providing a first control signal to said variable rate pulse generating means for varying the rate at which said stimulating pulses are produced thereby, the improvement comprising:
(a) means coupled to said pulse generating means and automatically responsive to the hemodynamic performance of the heart for limiting the upper rate to which said stimulating pulses can be driven by said first control signal.

9. The rate adaptive pacemaker as in claim 8 wherein said means for limiting the upper rate at which said stimulating pulses can be driven comprises:
(a) further means for sensing when an increase in stimulating rate is accompanied by a decrease in cardiac output; and
(b) means responsive to said further sensing means for inhibiting a further increase in said stimulating rate.

10. The rate adaptive pacemaker as in claim 9 wherein said means for limiting comprises:
(a) mans for sensing cardiac output of the heart and producing a second control signal proportional thereto; and
(b) logic means coupled to receive said first and second control signals for inhibiting said first control signal when said first control signal is determined to be in a direction to increase the stimulation rate when said second control signal is indicative of a decrease in cardiac output.

11. The rate adaptive pacemaker as in claim 10 wherein said means for sensing physiologic demand senses a different parameter than said means for sensing cardiac output.

12. The rate adaptive pacemaker as in claim 8 wherein said means for limiting comprises:
(a) logic means for detecting when the rate of change of cardiac output with respect to stimulation pulse rate drops below a predetermined slope value; and
(b) means responsive to said logic means for inhibiting said first control signal from increasing said stimulation pulse rate.

13. The rate adaptive pacemaker as in claim 8 wherein said means for limiting comprises:
(a) means for sensing physiologic demand for controlling stimulation pulse rate;
(b) means for sensing hemodynamic performance; and
(c) means responsive to said hemodynamic performance for inhibiting said first control signal from increasing said stimulation pulse rate.

* * * * *